United States Patent [19]
Mori et al.

[11] Patent Number: 6,162,786
[45] Date of Patent: Dec. 19, 2000

[54] BACTERIAL INFECTION-PREVENTIVE AGENT FOR FISH AND SHELLFISH LARVAE, AND METHOD FOR BREEDING THEM

[75] Inventors: Katsuyoshi Mori; Keisuke Takahashi, both of Sendai, Japan

[73] Assignee: Oyster Research Institute, Sendai, Japan

[21] Appl. No.: 09/197,529

[22] Filed: Nov. 23, 1998

[51] Int. Cl.[7] .......................... A61K 38/00; A61K 38/43; C12N 9/50
[52] U.S. Cl. .......................... 514/2; 424/94.1; 424/94.64; 424/94.67; 435/184; 435/219
[58] Field of Search .................. 514/2; 424/94.1, 424/94.64, 94.67; 435/184, 219

[56] References Cited

U.S. PATENT DOCUMENTS

| | | | |
|---|---|---|---|
| 4,759,933 | 7/1988 | Uchida et al. | 426/7 |
| 5,013,568 | 5/1991 | Corier et al. | 426/332 |
| 5,976,858 | 11/1999 | Palmer et al. | 435/219 |

*Primary Examiner*—Christopher S. F. Low
*Assistant Examiner*—Abdel A. Mohamed
*Attorney, Agent, or Firm*—Burns, Doane, Swecker & Mathis, LLP

[57] ABSTRACT

A new effective bacterial infection-preventive agent for fish and shellfish larvae is provided. This agent contains a protease inhibitor such as ovomacroglobulin, α 2-macroglobulin or an analog thereof.

10 Claims, 1 Drawing Sheet

Change in survival rate of Japanese oyster larvae artificially infected with V. tubiashii, and effect of ovoG to control the infection (final conc. of ovoG : 5μg/ml)

Change in survival rate of Japanese oyster larvae artificially infected with V. tubiashii, and effect of ovoG to control the infection (final conc. of ovoG : 5μg/ml)

BACTERIAL INFECTION-PREVENTIVE AGENT FOR FISH AND SHELLFISH LARVAE, AND METHOD FOR BREEDING THEM

BACKGROUND OF THE INVENTION

The present invention relates to a bacterial infection-preventive agent for fish and shellfish larvae, particularly marine fish and shellfish larvae and, among them, shells such as abalones (ear shells), oysters and scallops for preventing them from the bacterial infection while they are bred, and also to a method for breeding them.

The most popular method for counteracting the bacterial infection of fishes and shellfishes while they are bred in water is the administration of antibacterial agents such as antibiotics. For example, it was proved that some antibiotics have a high bacteriocidal effect on pathogenic bacteria (mainly vibrio) which harm bivalve larvae.

There is another method for breeding them in running water. For example, bivalve larvae are bred in a method wherein water for the larvae is not moved. That is, they are bred in a tank which is once filled with water, without pouring fresh water and without circulation or filtration of the water, and the whole water is changed periodically in order to keep it clean. The running water method is considered to be effective in preventing the propagation (abnormal growth) of the bacteria because fresh water can be always fed.

Although effects of preventing the bacterial infection can be expected to some extent in the both of the above-described methods, these methods still have problems described below.

Although the antibacterial agents have a remarkable effect of killing pathogenic bacteria, they also change the bacterial flora which contributes to the stabilization of the quality of the water in the tank. In such a water tank, bacteria are usually contained in an order of a million per ml of the water. It is known that when an antibiotic is thrown into the water, the number of the bacteria is reduced to about 1/1000 to 1/10,000 in a short time and that 24 hours after stopping the addition of the antibiotic, the number of the bacteria is increased again to the former level. Namely, some kinds of bacteria which are sensitive to the antibiotic are killed and other kinds of bacteria survive and propagate. When the bacterial florae composed of various kinds of bacteria, wherein the bacteria control each other and thereby keep the stable state of the bacteria, are decomposed and only a few kinds of the bacteria propagate, there is a high possibility of the occurrence of undesirable phenomena such as secondary infection and extreme reduction in the activity of the larvae. Another problem occurs in that when the antibacterial agent is used for a long time or repeatedly, drug-resistant bacteria will appear.

On the other hand, the running-water method is suitable for breeding the larvae and it has some merits, but it also has defects. Namely, from the viewpoint of the counteraction against the bacterial infection, the larvae-breeding conditions thereof are unsuitable (as compared with those of the not-moving water method) for the propagation of bacteria. However, when the larvae once suffer from some disease, there is substantially no countermeasure. In other words, since the stable bacterial flora is not formed in the tank in this method, the mutual controlling effect of the bacteria is unexpectable. In addition, the above-mentioned administration of an antibacterial agent is impossible. Only one method for protecting them from death from the mass infection is to keep a high activity of the larvae by continuously feeding water of a high quality so as to realize a high anti-microbial power of the larvae. If bacteria having a very strong pathogenicity propagate and the larvae have started to die, the control will be more difficult than in the not-moving water method.

Thus, in all the treating methods in the prior art, the mechanism of the bacterial infection or the mechanism of the appearance of the pathogenicity was substantially not taken into consideration. Namely, in all the methods, efforts are made only for the purpose of eliminating or reducing the bacteria in the water tank. For finding an effective method for preventing the infection or an effective treating method, not only the bacteria per se but also the pathogen and the mechanism of the infection should be elucidated, and also investigations should be made on the effective method against respective elements which cause the disease. Under these circumstances, the development of an effective method for preventing the bacterial infection of larvae of fishes and shellfishes is demanded.

SUMMARY OF THE INVENTION

The object of the present invention is to provide new effective bacterial infection-preventive agents for fish and shellfish larvae.

Another object of the invention is to provide an efficient method of breeding fish and shellfish larvae by protecting the larvae from the bacterial infection in the course of the breeding.

These and other objects of the present invention will be apparent from the following description and Examples.

The present invention has been developed on the basis of a finding that protease inhibitors are extremely effective in protecting fish and shellfish larvae from the bacterial infection.

Namely, the present invention provides a bacterial infection-preventive agent for fish and shellfish larvae, which comprises a protease inhibitor.

The present invention also provides a method of breeding fish and shellfish larvae, which comprises the step of breeding the larvae in the presence of the bacterial infection-preventive agent for fish and shellfish larvae in a breeding solution.

The present invention further provides a method of breeding fish and shellfish larvae, which comprises the steps of sufficiently aerating an aqueous solution for breeding the larvae with oxygen or air to saturate the solution with oxygen, and then breeding the larvae in the presence of the bacterial infection-preventive agent for the larvae without the aeration.

DESCRIPTION OF THE PREFERRED EMBODIMENTS

Figure 1:
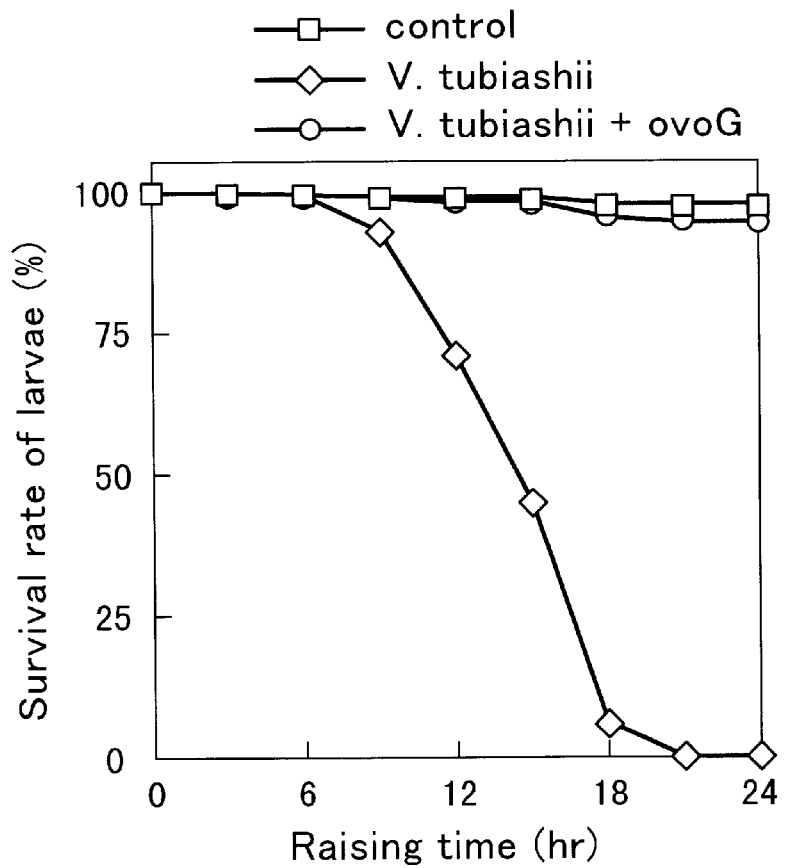
FIG. 1 shows the effect (in terms of the survival rate) of the bacterial infection-preventive agent of the present invention in breeding larvae of Japanese oysters.

The fish and shellfish larvae to be bred by the method of the present invention are those of various kinds of freshwater fishes and seawater fishes, preferably larvae of marine fishes and shellfishes. Among them, shellfishes (particularly bivalves) such as abalones, oysters and scallops and shrimps such as prawns are preferred. The larvae having a size of not larger than 300 $\mu$m are preferred in the present invention.

Examples of the protease inhibitors usable in the present invention include inhibitors effective against various proteases. Among them, serine protease inhibitors, metalloprotease inhibitors and cysteine protease inhibitors are preferred. The serine protease inhibitors include those derived from animals (which inhibitors have a high reaction specificity; the reaction being reversible) such as α 1-antitrypsin, antichymotrypsin, antithrombin, α 2-antiplasmin, plasminogen-activator inhibitors, pancreatic trypsin inhibitors and hirudine; serine protease inhibitors derived from vegetables and microorganisms (which inhibitors also have a high reaction specificity; the reaction being reversible) such as trypsin inhibitors, subtilisin inhibitors, leupeptin, chymostatin and elastatinal; serine protease inhibitors derived from organisms (which inhibitors inhibit various kinds of proteases; the reaction being irreversible, when the inhibitors are once bonded with an enzyme, the enzyme is deactivated) such as α 2-macroglobulin and ovomacroglobulin; benzamidine; aminocaproic acid; tranexamic acid; and peptide chloromethine ketones and the like. The metalloprotease inhibitors include chelating agents for metals, such as EDTA, phenanthroline and DTPA; and metalloprotease inhibitors derived from organisms such as α 2-macroglobulin, ovomacroglobulin and collagenase inhibitors (TIMP). The cysteine protease inhibitors include those derived from organisms such as stefine, cystatin and kininogen. They are usable either alone or in the form of a mixture of two or more of them.

Among the above-described protease inhibitors, ovomacroglobulin, α 2-macroglobulin and analogs thereof are preferred from the viewpoints of the safety and effect of inhibiting the bacteria from the propagation. The term "ovoglobulin" is a generic name for proteins contained in the egg whites of birds. When proteins are separated from egg whites, the ovoglobulins are contained in the globulin fraction. The amount of the ovoglobulins is about 10% based on the proteins in the eggwhite. The main component of the ovoglobulins is ovomacroglobulin. It has a molecular weight of about 720,000, and a tetramer structure consisting of four sub-units each having a molecular weight of about 180,000. It was already elucidated that this functional molecule is homologous to α 2-macroglobulin which is a strong protease inhibitor contained in the bloods of higher animals. The analogs include macroglobulins having a molecular weight of about 100,000 to 200,000.

The amount of the bacterial infection-preventive agent of the present invention for fish and shellfish larvae to be added to the aqueous solution or seawater in which the larvae are bred is variable depending on the kind of the larvae to be bred. It is such that the amount of the protease inhibitor will be preferably about 1 mg to 100 mg, more preferably about 5 mg to 50 mg, and most preferably about 10 to 30 mg, per kg of the aqueous solution or seawater.

The bacterial infection-preventive agent of the present invention may be previously dissolved in the aqueous solution or seawater for breeding the larvae; or it may be dissolved in the aqueous solution or seawater after the fish or shellfish larvae were put therein; or a previously prepared solution of the bacterial infection-preventive agent may be added thereto. It is thus preferred to breed the fish or shellfish larvae in the aqueous solution or seawater containing the bacterial infection-preventive agent of the present invention. In a preferred method, an aqueous solution in a water tank used for breeding the fish or shellfish larvae is sufficiently aerated with oxygen or air to saturate the water with oxygen before the larvae are put into the tank, then the bacterial infection-preventive agent of the present invention is dissolved therein, and the larvae are put therein and bred without the aeration while the aqueous solution is exchanged everyday or every several days in the course of the breeding. Although bubbles are formed in another method wherein air is introduced into the tank through an air stone or the like during the breeding, such a bubble formation can be controlled by the method of the present invention, and the effect of preventing the bacterial infection can be efficiently maintained in the above-mentioned preferred method.

The specific description will be made below on the present invention with reference to a case wherein Japanese oyster (Crassostrea gigas) larvae are used as the shellfish larvae. 70 l of seawater (temperature: about 22° C.) is fed into a 100 l water tank. Oxygen is introduced into the seawater from an oxygen bomb through a pipe for about 5 to 10 minutes to saturate the seawater with oxygen. Then the bacterial infection-preventive agent of the present invention is dissolved therein by stirring so that the concentration of the protease inhibitor is about 0.005 to 0.01% by weight. About 1,000 to 2,000 Japanese oysters are placed per liter of the water and bred therein without aeration for one or several days. Then the oysters are transferred into seawater, in which the bacterial infection-preventive agent of the present invention is dissolved and which is prepared in the same manner as that described above, to continue the breeding.

The present invention can provide the new effective bacterial infection-preventive agent for fish and shellfish larvae. By using the bacterial infection-preventive agent for larvae, the larvae of various kinds of fishes and shellfishes can be efficiently bred.

The following Examples will further illustrate the present invention.

EXAMPLE 1

5 l of seawater was fed into a small-sized water tank of 7 l. Larvae of Japanese oysters (about five days after the hatching; having an average shell height of 150 μm) were put into the tank in a density of one larva/ml. The seawater in the tank was inoculated with Vibrio tubiashii (ATCC 19106; the final density: 100,000 CFU/ml) which is a strong pathogenic bacterium. Immediately thereafter, ovoglobulins (derived from chicken egg whites) which are experiment reagents of Sigma (U.S.A.) were dissolved therein in such an amount that the final concentration thereof would be 5 μg/ml. The larvae were bred at a water temperature of 21 to 23° C. and the survival rate of them was determined at intervals of three hours.

The same breeding tests were repeated except that ovoglobulins were not used (Comparative Example) or that the inoculation with Vibrio tubiashii was omitted and ovoglobulins were not used (Control), and the survival rate of the larvae was determined at intervals of three hours.

The results are summarized in FIG. 1. It is apparent from the results that in a group wherein only the bacteria were used (Comparative Example), shells began to die about 12 hours after, and the death rate rapidly increased 15 hours after and reached 100% 21 hours after. On the other hand, in a group wherein ovoglobulins were also used (present invention), the dead shells were scarcely found, more than 90% of the shells survived after 24 hours, and no abnormality was recognized in the motion of them.

EXAMPLE 2

The breeding tests were conducted for one week in the same manner as that of Example 1 except that a 100 l water tank and 70 l of seawater were used. The survival rate and growth of the larvae were compared with those of the control group. Water was exchanged every two days. As a result, the effect of the present invention was evident as in the test conducted in the small tank.

EXAMPLE 3

70 l of seawater was fed into a 100 l water tank. The seawater was saturated with oxygen by introducing oxygen therein from an oxygen bomb through a pipe for about 5 to 10 minutes. Then the same ovoglobulins as those used in Example 1 were dissolved therein under stirring so that the final concentration thereof would be 10 $\mu$g/ml. Larvae of Japanese oysters (about three days after the hatching; having an average shell height of 100 to 110 $\mu$m) were put into the tank in a density of one larva/ml. The seawater in the tank was inoculated with Vibrio tubiashii (ATCC 19106; the final density: 100,000 CFU/ml). The larvae were bred at a water temperature of 21 to 23° C. for one or several days and then transferred into seawater containing the bacterial infection-preventing agent of the present invention dissolved therein. After continuing the breeding for one week, the survival rate and growth of them were the same as those of the controls.

What is claimed is:

1. The method of breeding shellfish larvae which comprises breeding the larvae in the presence of a breeding solution comprising a bacterial infection inhibiting ovomacroglobulin for a time and under conditions to inhibit bacterial infection.

2. The method of claim 1, wherein the breeding solution contains ovomacroglobulin in an amount of about 1 mg to 100 mg per kg of the solution.

3. The method of claim 1, wherein the shellfish larvae are selected from the group consisting of abalones, oysters and scallops.

4. The method of claim 3, wherein the shellfish larvae are oyster larvae.

5. The method of claim 4, wherein the oyster larvae are Japanese oyster larvae.

6. A method of breeding shellfish larvae which comprises aerating an aqueous solution used to breed the larvae with oxygen or air to produce an oxygen saturated solution, and then breeding the larvae in the presence of a bacterial infection inhibiting ovomacroglobulin.

7. The method of claim 6, wherein the breeding solution contains ovomacroglobulin in an amount of about 1 mg to 100 mg per kg of the solution.

8. The method of claim 6, wherein the shellfish larvae are selected from the group consisting of abalones, oysters and scallops.

9. The method of claim 8, wherein the shellfish larvae are oyster larvae.

10. The method of claim 9, wherein the oyster larvae are Japanese oyster larvae.

* * * * *